(12) United States Patent
Thong

(10) Patent No.: US 6,553,261 B2
(45) Date of Patent: Apr. 22, 2003

(54) SIGNALING METHOD FOR AN IMPLANTABLE CARDIAC STIMULATION DEVICE AND A CARDIAC STIMULATION DEVICE

(75) Inventor: Tran Thong, Portland, OR (US)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 6 days.

(21) Appl. No.: 09/872,159

(22) Filed: Jun. 1, 2001

(65) Prior Publication Data

US 2002/0022865 A1 Feb. 21, 2002

(30) Foreign Application Priority Data

Jun. 5, 2000 (DE) .......................... 100 28 095

(51) Int. Cl.[7] ................................ A61N 1/37
(52) U.S. Cl. ........................................ 607/27
(58) Field of Search .................. 607/27, 28, 29, 607/9

(56) References Cited

U.S. PATENT DOCUMENTS

| 4,276,883 A | 7/1981 | McDonald |
| 4,488,555 A | 12/1984 | Imran |
| 5,899,928 A | 5/1999 | Sholder |
| 5,944,746 A | 8/1999 | Kroll |
| 6,067,469 A | 5/2000 | Kim |

FOREIGN PATENT DOCUMENTS

| DE | 33 44 642 C2 | 6/1984 |
| DE | 42 13 993 A1 | 12/1992 |
| EP | 0 665 032 A2 | 8/1995 |
| EP | 0 670 170 A1 | 9/1995 |
| EP | 0 972 540 A2 | 1/2000 |

Primary Examiner—Scott M. Getzow
(74) Attorney, Agent, or Firm—Hahn Loeser + Parks LLP; Stephen L. Grant

(57) ABSTRACT

The invention concerns a method of signaling an internal status of an implantable cardiac stimulation device, which status is defined by a value of a status parameter, including the steps: a) Recording a measurement value (S12) representing the status parameter, b) Ascertaining the existence of the status by comparison of the measurement value with a comparative value (S14), c) Delivering a signal pulse with a predetermined, measurable pulse parameter, wherein the pulse parameter is uniquely associated with the status if the measurement value corresponds to the comparative value within predetermined limits (S26). In accordance with the invention the time difference of equal, predetermined phases of two successive, periodically recurring events prior to delivery of the signal pulse is measured (S20), and then the signal pulse is delivered prior to or after the next expiry of the measured time difference by a predeterminable period of time uniquely associated with the status (S22, S24, S26). The invention further concerns a cardiac stimulation device for carrying out that method.

67 Claims, 4 Drawing Sheets

SIGNALING METHOD FOR AN IMPLANTABLE CARDIAC STIMULATION DEVICE AND A CARDIAC STIMULATION DEVICE

The invention concerns a method of signaling an internal status of an implantable cardiac stimulation device, which status is defined by a value of a status parameter, as set forth in the classifying portion of claim 1. The invention further concerns a cardiac stimulation device as set forth in the classifying portion of claim 10.

BACKGROUND OF THE ART

Methods and apparatuses for external recognition of the technical status of an implantable cardiac stimulation device are known, which make it possible to take the desired information about the technical status from the stimulation pulses which are delivered by the device. In particular, U.S. Pat. No. 5,899,928 discloses a signaling method in which the item of information to be communicated is encoded as a defined period of time between two successive stimulation pulses. After a measurement value representing a status parameter has been recorded, it is associated by comparison with one of three comparative value intervals. Associated with each of those comparative intervals is a defined pulse spacing in respect of time, of 500, 600 or 700 ms. Delivery of signal pulses of that kind is effected after detection of an external magnetic field. In order to clearly identify a subsequent pulse or a subsequent pulse sequence as signaling pulses, a "synchronization pulse" which is not described in greater detail is previously produced. A disadvantage with that method is that it can only be used when the natural cardiac rhythm is totally nullified by the use of pacemaker therapy. A method of that kind cannot therefore be used in relation to a "demand" pacemaker or cardioverter/defibrillator because in that case stimulation pulses are delivered only in situations in which the status of the heart, which is monitored by a measurement procedure, requires that.

SUMMARY OF THE INVENTION

The object of the present invention is to provide a method and a cardiac stimulation device of the kind set forth in the opening part of this specification, which do not suffer from the stated disadvantages.

In terms of a method of the kind set forth in the opening part of this specification, that object is attained by a method of signaling an internal status of an implantable cardiac stimulation device, which status is defined by a value of a status parameter, including the following steps:

a) recording a measurement value representing the status parameter, b) ascertaining the existence of the status by comparison of the measurement value with a comparative value, c) measuring the time difference of equal, predetermined phases of two successive, periodically recurring sequences of events, and d) delivering at least one signal pulse with a predetermined, measurable pulse parameter, if the measurement value corresponds to the comparative value within predetermined limits, wherein the pulse parameter is uniquely associated with the status by the delivery of the signal pulse being effected prior to the next expiry of the measured time difference by a predeterminable period of time uniquely associated with the status.

The method according to the invention provides that the moment in time of delivery of the signal pulse is coupled to a predetermined phase of a periodically recurring sequence of events. The term sequence of events is used to denote a number of events which occur in succession in respect of time. A phase of that sequence of events is defined by a given one of those events. The moment in time at which the phase occurs is the moment in time at which that given event occurs. The spacing in respect of time between the individual events of the sequence of events can vary from one period to another so that the duration of the sequence of events, that is to say of a period, can also be variable each and every time. This is an essential advantage of the method according to the invention: there is no need for coupling of the moment in time of delivery of the signal pulse, to a predetermined period duration. Implementation of the method according to the invention is not bound to predetermined boundary conditions in regard to period duration and can thus be used in a more variable fashion.

The current period duration is measured in the course of implementation of the method with step c) only shortly before delivery of the signal pulse. For that purpose, the time difference of two predetermined, identical phases of successive periods is determined. The later one of those two phases is within the last, completely passed period, prior to delivery of the signal pulse. Determining the moment in time of delivery of the signal pulse relative to the periodic sequence of events is based on the measured moment in time of the last occurrence of the predetermined phase, the measured period duration and the predetermined time displacement.

The predetermined, measurable pulse parameter which serves for signaling purposes is a time displacement in respect of delivery of the signal pulse with respect to the occurrence of the given phase of the periodic sequence of events.

The method is preferably used in relation to an implantable cardiac stimulation device. However, implantation of the device in the human body is neither a partial step in nor a necessary prerequisite for executing the method according to the invention. The method can equally be used in relation to a non-implanted cardiac stimulation device, for example for test purposes in the context of quality control immediately after manufacture or immediately prior to an implantation procedure.

The periodically recurring sequence of events can be internal or external in relation to the implantable cardiac stimulation device. Delivery of the signal pulse can for example be coupled to a periodic clock signal which is an internal signal, that is to say which is produced in the cardiac stimulation device, and the frequency of which is presettable, that is to say independent of the duration of a cardiac period. That frequency can also be variable.

In preferred embodiments of the invention the signal pulse is delivered in time relationship with a periodically recurring sequence of events which is external, that is to say which is produced outside the cardiac stimulation device. This involves for example an external ultrasonic pulse which is detected by means of an ultrasonic sensor integrated in the cardiac stimulation device. The ultrasonic sensor produces a pulsed electrical signal corresponding to the ultrasonic pulse. The time difference of equal, predetermined phases of two successive pulses of that electrical signal is measured and used for control in respect of time of the subsequent delivery of the signal pulse.

In a particularly preferred embodiment of the invention the periodically recurring sequence of events is coupled to cardiac activity. The sequence of events can be for example the occurrence of a defined phase of a measurement signal which reflects the time pattern or variation in cardiac activity. In this respect, it is already sufficient if that measurement signal only reflects the onset of a given phase of cardiac activity. In this connection, c) of the method of the invention involves measurement of the time difference of equal, predetermined phases of two successive cardiac periods prior to delivery of the signal pulse. In terms of the implementability of the method according to the invention, it is immaterial whether the cardiac activity is stimulated or natural.

Measurement of the time difference of equal, predetermined phases of two successive cardiac periods is effected here solely to determine the moment in time of the subsequent delivery of the signal pulse, in accordance with step d) of the method. The measurement data obtained are not used to produce a medical diagnosis in respect of cardiac activity, but serve solely for technical purposes.

It will be appreciated however that the measurement data obtained with step c) of the method can be used for diagnostic measures. Such diagnostic measures however are not related to the claimed method which is concerned solely with signaling an internal technical status of a cardiac stimulation device. Such an internal status is defined for example by a value of the output voltage of an accumulator, or the electrical resistance of an electrical conductor between components of the cardiac stimulation device.

It will be appreciated that surgical, diagnostic or therapeutic measures which lie outside the claimed method can open up further profitable possible uses of the method according to the invention. For example the signaling method according to the invention can be used in a cardiac stimulation device in order to signal cardiac arrhythmia phenomena such as tachycardia which are detected by a diagnostic process which is not subject-matter of this application, in response to an external inquiry.

Known therapeutic measures also open up areas of use to the signaling method according to the invention. For example the method according to the invention can be used in a cardiac stimulation device which is designed to implement "on-demand" pacemaker therapy. Depending on whether pacemaker therapy is or is not implemented at the moment in time of signaling, two situations are possible. In one situation the signal pulse is delivered subsequently to cardiac stimulation pulses which are produced in the course of the pacemaker therapy. In the other possible situation delivery of the signal pulse occurs in a period of time in which the heart beats independently without the application of therapy. In both situations delivery of the signal pulse is outside the therapeutic measures. It is here that an essential advantage of the method according to the invention manifest itself: it operates independently of whether cardiac activity is stimulated or natural.

The signal pulses can be delivered to the cardiac muscle in the form of electrical current pulses by way of a stimulation electrode of the cardiac stimulation device. The signal pulses can be uniquely distinguished from the cardiac stimulation pulses delivered in the context of pacemaker therapy, by virtue of the moment in time at which the pulses are delivered. That moment in time is determined in accordance with steps c) and d) of the method according to the invention.

A preferred embodiment of the method according to the invention is started as soon as a triggering signal is present in the cardiac stimulation device. As long as the triggering signal is not present, the method is not started. Production of the triggering signal is preferably coupled to an external event or an external status change. For example, the triggering signal can be produced if a magnetic field or an ultrasonic signal involving predetermined parameters are detected at the location of the cardiac stimulation device. Such an event can indicate for example the reception readiness of a receiver for the signal pulse.

If the triggering pulse is still present after the signaling method has been carried into effect, the signaling method in a further embodiment is carried into effect again. In that way, correct reception of the signal pulse can be checked on the part of the receiver. Particularly besides a pacemaker therapy process, repeated implementation of the method promotes certainty of the correct interpretation of the signal pulse. For, signaling of the internal status of the cardiac stimulation device can be detected by virtue of the time displacement of the signal pulse in comparison with the time spacing of two immediately preceding cardiac stimulation pulses. A slight time displacement however can be difficult to resolve in terms of measurement procedures and can be such that it can only be uniquely identified after repeated delivery of the signal pulse.

A further embodiment of the method according to the invention is distinguished in that, subsequently to delivery of the signal pulse, for a predeterminable number of subsequent sequences of events, no signal pulse is produced. If the triggering signal is present over a relatively long period of time, that results in a periodically repeated series of events which includes the predetermined number of periodic events and a subsequent signal pulse. That series of events is repeated as long as the triggering signal is present. The benefit of that embodiment is that the signal pulse can be more easily recognized by virtue of its repetition after a regular, predetermined number of events.

Typically, the predetermined number of events between the signal pulses is five. Preferably, the invention provides for external programmability of that number so that for example it can be variably preset between two and twelve.

In a further embodiment of the signaling method according to the invention a physical parameter which is dependent on the phase in the cardiac cycle is measured. Preferably, an electrocardiogram is recorded. Recording of the electrocardiogram can be effected by means of separate electrodes or, in the case of implanted cardiac stimulation unit, by means of the stimulation electrodes. The time difference of equal phases of two successive cardiac periods can be measured in known manner by reference to an electrocardiogram. In this embodiment—as was discussed in detail hereinbefore—recording of the electrocardiogram does not serve for any diagnostic purposes whatsoever, but only for near-time pre-determination of the moment in time for delivery of the signal pulse, corresponding to step d) of the method according to the invention.

At the present time use of the method according to the invention is preferred in an embodiment in which the measurement value which is to be recorded and which represents the status parameter is an electrical voltage which occurs at the output of an energy storage means arranged in the cardiac stimulation device. The output voltage of the energy storage means is recorded as a measurement in respect of its energy content. If in the passage of time the output voltage falls to or below a predetermined comparative value, a signal pulse is generated when the triggering signal is present. In that way, the presence of internally registered statuses of the energy storage means such as "EOL" (end-of-life) or "ERI" (elective-replacement-indication) becomes accessible to external recognition which can be easily implemented, for example in the course of a routine check in the practice of a general practitioner.

Referral to a specialist is only required when the presence of one of those statuses has actually been signaled.

In regard to a cardiac stimulation device, the object of the invention is attained by a cardiac stimulation device comprising a pulse generator which is adapted to produce pulses suitable for cardiac stimulation, at least one stimulation electrode connected to the pulse generator and adapted to deliver the pulses, a signal generator connected to the pulse generator and adapted to produce and delivery pulse triggering signals at defined moments in time, a cardiac phase measurement sensor adapted to record a first measurement value dependent on the current phase of the cardiac cycle, time measurement means connected to the cardiac phase measurement sensor and adapted to determine a cycle duration between the occurrence of a predetermined phase of a defined first cardiac cycle and the occurrence of the same phase of the immediately successive, second cardiac cycle, and time matching means which are connected to the time measurement means and on the output side to the signal generator and which are adapted to predetermine the period of time between the occurrence of the predetermined phase of the second cardiac cycle and the subsequent production of a pulse triggering signal.

The cardiac stimulation device according to the invention has time matching means. They receive from the time measurement means a cycle duration signal which corresponds to the duration of the cardiac period which last elapsed.

In this respect, the term duration of a cardiac period is used to denote the time difference between the occurrence of a given phase in a cardiac cycle and the occurrence of the same phase in the immediately subsequent cardiac cycle. The operation of determining the spacing in respect of time between identical phases of successive cardiac periods is carried into effect for example on the basis of the occurrence of R-spikes. The simplest thing however is to measure the time interval between the Q-spikes. Measurement of the period duration is started and stopped with the attainment of a predetermined voltage threshold value which in the present embodiment is negative. That time measurement method operates reliably both in relation to natural and also to stimulated cardiac activity.

On the basis of the cycle duration signal, the time matching means predetermines the period of time which will elapse from the end of the measured cardiac period, that is to say from the last occurrence of the given phase, to the subsequent production of a pulse triggering signal.

The cardiac stimulation device according to the invention, by virtue of the time matching means, is capable of predetermining the moment in time of subsequent production of a signal pulse after a stimulated and in particular also after a natural, non-stimulated cardiac activity. The question of whether the cardiac period whose duration was determined by virtue of the time measurement means came about due to a stimulated or a non-stimulated, natural cardiac activity, is immaterial in regard to subsequent signaling.

In the case of the device according to the invention a signal pulse is a pulse which is suitable for cardiac stimulation. Preferably the signal pulse is in the form of a ventricular stimulation pulse. The signal pulse is the same in terms of its pulse parameters such as voltage and duration as the cardiac stimulation pulses which are usual in the context of pacemaker therapy, apart from the moment in time at which it is delivered. The signal pulse differs from stimulation pulses by virtue of its displacement in respect of time relatively to the current phase position of the cardiac activity.

The moment in time at which a signal pulse is produced is predetermined in the case of the cardiac stimulation device according to the invention only shortly before it is triggered off. Directly after the cardiac period which last elapsed, the duration thereof having been determined by the time measurement means for example on the basis of the QQ-time interval, the moment in time of delivery of the signal pulse is calculated by means of the time matching means.

The period of time between the end of the last cardiac period, for example the last Q-spike, and the moment in time of delivery of the signal pulse, which is predetermined by the time matching means, differs from the measured period duration by a significant, measurable time difference. In that way, it is possible to produce a signal pulse which is matched in respect of its delivery time to the instantaneous cardiac period duration, and in that respect therefore it is "synchronized". For it is to be assumed that the cardiac period duration changes only insignificantly from one period to the next.

The device according to the invention is therefore not reliant on a fixed stimulation rhythm, with a departure therefrom for the signaling procedure. On the contrary, it is adapted by way of the time matching means in the production of a signal pulse to the instantaneous and possibly natural cardiac rhythm. That is a matter of great significance in particular in relation to defibrillator patients as they could react to asynchronous production of cardiac stimulation pulses, with a cardiac arrhythmia. The quasi-synchronous production of a cardiac stimulation pulse which serves for signaling purposes, by means of the device according to the invention, avoids that risk.

In the case of the cardiac stimulation device according to the invention the time matching means are adapted to cause the delivery of a signal pulse, that is to say a time-displaced cardiac stimulation pulse, immediately after measurement of the duration of a cardiac period. In regard to the choice of the time displacement, on the one hand account is to be taken of the fact that the time displacement can be externally detected. Therefore the time displacement should be sufficiently great that doctors or medical personnel can identify a time-displaced stimulation pulse by way of evaluation of an ECG, more specifically both in relation to otherwise natural cardiac activity and also in relation to stimulated cardiac activity. On the other hand, the time displacement of the signal pulse is to be so selected that the risk of triggering off a cardiac arrhythmia by the signal pulse, if not completely avoided, is nonetheless kept down at a particularly low level. Making it possible to provide for matching in respect of time of the signal pulse in relation to the current phase position of the cardiac activity, whether stimulated or non-stimulated, in order to avoid stimulation in a vulnerable phase, is a major advantage of the invention. The signal pulses are preferably delivered in the form of premature ventricular stimulation pulses.

The time matching means provide for delivery of the signal pulse, which is phase-matched in relation to the cardiac period. For that purpose, they access the measurement values in respect of the period duration, which are produced by the time measurement means. As the time measurement means measure the period duration on the basis of the occurrence of a given phase of cardiac activity, the phase position of the cardiac activity is also determined, with the phase duration. The time matching means use both items of information for careful gentle delivery of signal pulses.

Signal pulse delivery, which is not pro-arrhythmic, is ensured if the moment in time of delivery of the signal pulse avoids the vulnerable phase of the ventricular cardiac cycle. The vulnerable phase of the cardiac chambers approximately coincides with the rising edge of the T-wave of the ECG.

Hereinafter the details relating to the time displacement of the signal pulse are based on the moment in time, as determined by the time measurement means, of the last occurrence of the Q-spike. It will be appreciated however that the value of the time displacement would be different if measurement of the cardiac period duration were based on another phase in cardiac activity. What is important is the phase position, as determined by such details, of the moment in time of delivery of the signal pulse relative to the cardiac period.

In an embodiment, the time matching means are adapted to produce the pulse triggering signal which results in the production of the signal pulse by the pulse generator, no earlier than 300 ms prior to the expiry of the given cycle duration after the occurrence of the predetermined phase of the second cardiac cycle. That time displacement in relation to the current cardiac rhythm can be easily recognized in the surface ECG.

In a particularly preferred embodiment the premature cardiac stimulation pulse is produced no earlier than 200 ms prior to the expiry of the given cycle duration after the occurrence of the predetermined phase of the second cardiac cycle. Stimulation pulses which are delivered prematurely by between about 100 and 200 ms can also be easily detected in the surface ECG. In order to ensure detectability on the surface ECG, a premature cardiac stimulation pulse should be produced no later than 50 ms prior to the expiry of the given cycle duration after the occurrence of the predetermined phase of the second cardiac cycle.

A further embodiment of the apparatus according to the invention has a status measurement sensor which is connected to the time matching means and which is adapted to record at least one status measurement value which depends on the current value of a status parameter of the device. It is particularly borne in mind that the status measurement sensor is so adapted that the status measurement value depends on the energy content of an energy storage means of the device. However, other measurable status parameters can also be detected by a suitably designed status measurement sensor, for example the electrical resistance of stimulation electrodes connected to the device. Diagnostically ascertained states of the heart of the patient or given pathological events such as for example cardiac arrhythmia can also be detected by a status measurement sensor and signaled to the exterior by the cardiac stimulation device.

An embodiment includes a comparative value storage means for recording at least one comparative value for the status measurement value. In that case, monitoring of the status measurement value is preferably effected by first comparison means which are connected on the input side to the status measurement sensor and the comparative value storage means and on the output side to the time matching means. The comparison means are adapted to compare the status measurement value to the comparative value and to produce and deliver a status signal which is dependent on the comparison result.

If the status signal indicates that the status measurement value does not coincide with the comparative value within predetermined limits, the time matching means are activated. In an embodiment of the invention, activation of the time matching means is effected by means of a monitoring unit which is connected on the input side to the first comparison means and on the output side to the time matching means. The monitoring unit compares the status signal to at least one pre-stored reference status value range and produces a waiting signal if the status signal is not contained in the reference status value range. The waiting signal is transmitted to the time matching means.

In order to avoid the production of unnecessary signal pulses in situations in which no external receiver is ready to record the signal pulse, a further embodiment of the invention has an activation measurement sensor which is connected to the time matching means. The activation measurement sensor serves to receive measurement values (hereinafter referred to activation measurement values) of an activation measurement parameter. That can be for example a magnetic field strength as is produced by currently available external pacemaker testing units. It is only when the activation measurement sensor detects a magnetic field of predetermined field strength that in this embodiment the time matching means are activated.

Evaluation of the measurement values recorded by the activation measurement sensor, in a further embodiment, is effected by means of second comparison means which are connected at the output side to the monitoring unit. The second comparison means access a pattern value storage means. Pattern activation values can be stored in the pattern value storage means. These involve activation measurement values with given parameters to which is attributed the significance of reception readiness of an external receiver for the signal pulse. The second comparison means compare the current activation measurement value to the pattern activation value contained in the pattern value storage means. In the event of the activation measurement value coinciding with the pattern activation value, the comparison means produce a triggering signal which is received by the monitoring unit.

In this embodiment, the monitoring unit produces a waiting signal only when the status measurement value is outside its normal value range and at the same time the activation measurement value indicates that the signal pulse to be produced can be detected by an external receiver.

In an embodiment, the cardiac phase measurement sensor is adapted to pick up a measurement signal which is dependent on the electrical polarization of the myocardium, preferably to record an electrocardiogram. The cardiac phase measurement sensor can be provided specifically, that is to say for example in the form of one or more implanted derivation electrodes. Where possible however the stimulation electrodes are preferably at the same time in the form of cardiac phase measurement sensors and can therefore be used both to stimulate the heart and also to record an ECG.

A regular sequence of normal and time-displaced events facilitates identification of the signal pulse which is delivered by the stimulation device, in terms of evaluation of a surface ECG. In an embodiment which is designed for that purpose the device according to the invention has pacemaker control means which are connected to the time matching means and which are adapted for the selective production of an activation or a deactivation signal for respectively activating or deactivating operation of the time matching means. The pacemaker control means are preferably connected to the cardiac phase measurement sensor and are adapted to activate or deactivate operation of the time matching means for a predeterminable number of cardiac cycles. The number of cardiac cycles after a signal pulse is determined by evaluation of the measurement signal received from the cardiac phase measurement sensor.

In a preferred embodiment the pacemaker control means are additionally adapted to activate operation of the time matching means for the duration of only one cardiac cycle and for immediately subsequent deactivation. That ensures that the premature cardiac stimulation pulses are isolated, that is to say they are delivered subsequently to and followed by a predetermined number of natural cardiac periods or regularly stimulated cardiac stimulation pulses. This is to protect and carefully treat the patient as, after the production of a signal pulse, the system reverts immediately to natural cardiac activity or to regular stimulation. The duration of deactivation of operation of the time matching means is preferably between at least two and at most fifteen cardiac cycles. In an embodiment the number of cardiac cycles between two signal pulses can be altered by programming of the pacemaker control means from the exterior.

In another embodiment of the invention connected upstream of the pacemaker control means is a cardiac monitoring unit which is connected to the time measurement means and which is adapted to compare the respectively measured period duration to at least one reference cycle duration range which is contained in a reference cycle value storage means. The cardiac monitoring unit receives the measurement signal of the time measurement means, determines the period duration and compares it to the reference period duration range. In the situation where there is a deviation of the measured period duration from the reference period duration range, in a further embodiment of the invention the cardiac monitoring unit is adapted to produce a therapy warning signal which is dependent on the value of the deviation.

Preferably, the pacemaker control means are adapted to produce the deactivation signal and communicate it to the time matching means as soon as they receive a therapy warning signal from the cardiac monitoring unit. That avoids the delivery of premature cardiac stimulation pulses in such situations in which the cardiac rhythm deviates from normal values and premature cardiac stimulation pulses could trigger off or increase an arrhythmia situation.

In a further embodiment, the pacemaker control means are adapted to block the production of an activation signal for a defined period of time in the event of receiving a therapy warning signal. That ensures that pacemaker therapy which is primarily required is not interrupted by the delivery of premature stimulation pulses.

The cardiac stimulation device according to the invention has the advantage over the previously known arrangements that it can be carried into effect in many different design configurations. The particular advantages thereof can take effect in particular in a design configuration in the form of an "on-demand" pacemaker or an integrated cardioverter-defibrillator (ICD). An embodiment of the invention is in the form of ICD and has a cardioversion unit which is adapted to produce and deliver stimulation pulses suitable for cardioversion or defibrillation, at defined moments in time. The cardioversion unit is connected to the pacemaker control means which control activation or deactivation of the cardioversion unit.

In addition, a further embodiment of the invention, for carrying out a pacemaker therapy, has a trigger unit which is connected on the input side to the cardiac phase measurement sensor and on the output side to the signal generator and which is adapted to produce and deliver cardiac stimulation pulses at defined moments in time in the context of a pacemaker therapy. In this embodiment, the pacemaker control means preferably take over co-ordination between pacemaker therapy and signaling. The pacemaker control means are connected to the trigger unit and to the time matching means and are adapted to produce and deliver at least one activation or deactivation signal to the trigger unit or the time matching means. When an activation signal is delivered to the pacemaker unit, a deactivation signal is also delivered to the time matching means. Vice-versa, when an activation signal is delivered to the time matching means, a deactivation signal is also delivered to the trigger unit. The delivery of activation and deactivation signals, for the sake of simplicity, can also be replaced by a change-over switching device which is controlled by the pacemaker control means and which selectively activates the time matching means or the trigger unit. In that case, the trigger unit is connected in parallel with the time matching means. The signal generator is therefore actuated either by way of the time matching means or by way of the trigger unit.

In an apparatus with integrated pacemaker functions, for the sake of simplicity the signaling pulses are also produced by the pacemaker unit so that here it is possible to forego a signal pulse generator which is designed specifically for the production of signal pulses.

BRIEF DESCRIPTION OF THE DRAWINGS

Further embodiments of the method according to the invention and the device according to the invention are described hereinafter with reference to the drawings in which.

DETAILED DESCRIPTION OF THE INVENTION

Figure 1:
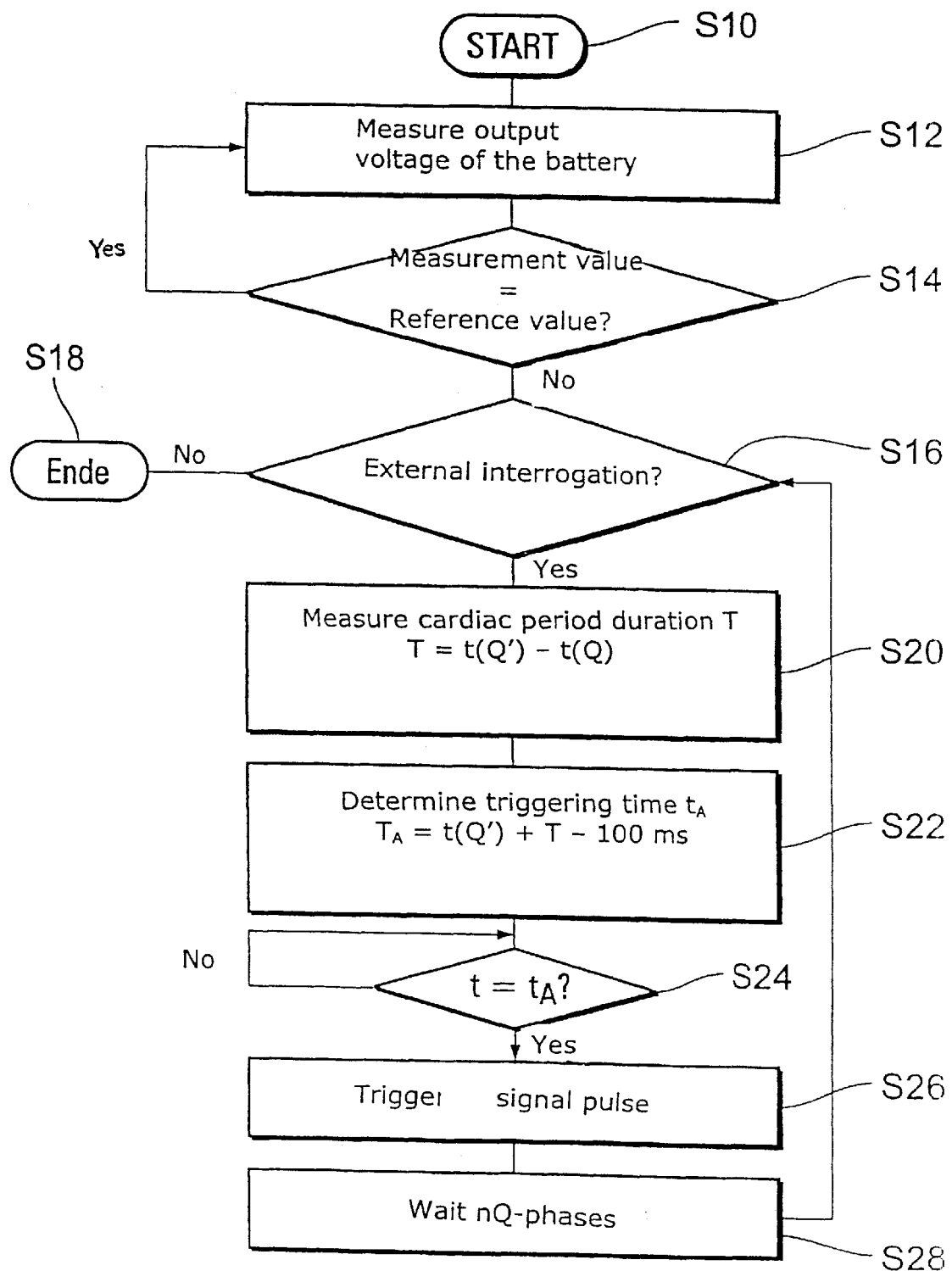
FIG. 1 shows a flow chart of an embodiment of the method according to the invention.

FIG. 1 is a flow chart showing an embodiment of the signaling method according to the invention.

The method is started with a step S10. In a subsequent step S12 the output voltage of a battery is measured as a status parameter. The battery serves for the supply of energy for an implantable cardiac stimulation device. In a subsequent step S14 the measured output voltage is compared to a reference or target voltage. It will be appreciated that, instead of a reference voltage, it is also possible to use a reference value range for the comparison procedure.

If the measurement value coincides with the reference value, then step S12 is carried out again. The loop formed by the steps S12 and S14 therefore serves for monitoring the battery voltage. Prior to renewed execution of the step S12 after a condition of coincidence has been detected between the measurement value and the reference value, it is also possible to pass through a waiting loop of predetermined duration.

If it is established in step S14 that the measured output voltage is not coincident with the reference value or the reference value range, then in a subsequent step S16 a check is made to ascertain whether there is a magnetic triggering signal. In an alternative embodiment, that method step S16 is additionally executed between the steps S10 and S12. In other words, in this embodiment, measurement of the output voltage is only executed in response to the magnetic triggering signal.

If no magnetic triggering signal can be detected the method is terminated with step S18. Alternatively, it is also possible to provide a waiting loop of prolonged duration, after the end of which a check is again made for the presence of the magnetic triggering signal.

The magnetic triggering signal is produced in known manner by applying an external programming and checking unit for the cardiac stimulation device to the chest of the patient. It will be appreciated however that implantation of the cardiac stimulation device is not a prerequisite for carrying the method into effect. The triggering signal can equally be detected if the cardiac stimulation device is not implanted.

If a magnetic triggering signal is detected, then in a step S20 the current cardiac period duration is determined as the time difference $$T = t(Q') - t(Q)$$

between two moments in time t(Q') and t(Q) of two successive cardiac periods, at each of which the curve passes through the respective voltage minimum of the Q-spike in the electrocardiogram.

It will be appreciated that, instead of the Q-spike of the ECG, it is also possible to refer to another phase in excitation of the myocardium in the cardiac cycle for the purposes of measuring the period duration. The electrocardiogram is recorded in known manner by means of the stimulation electrodes or measurement electrodes which are provided specifically for that purpose.

In a subsequent step S22 the moment in time $t_A$ at which a signal pulse is to be produced is calculated in advance. In this case, recourse is had to a predetermined time constant $\Delta t$. In the present example $\Delta t$ is 100 ms. The triggering time is determined in step S22 in accordance with the formula:

$$T_A = t(Q') + T - \Delta t$$

In that respect the sum t(Q')+T describes the hypothetical moment in time of the next occurrence of the Q-spike for the situation where the cardiac period remains unchanged. It will be appreciated that the precise moment in time of the occurrence of the next Q-spike basically cannot be determined in advance. The assumption of an identical period duration of two successive cardiac periods however represents a good assumption which is sufficiently accurate for the signal pulse to be externally recognizable. What is important is that the moment in time of the occurrence of a given cardiac phase is calculated in advance by means of that sum in step S22.

Then, with a step S24, the occurrence of the moment in time $t_A$ is awaited. A signal pulse is triggered at the time $t_A$ with a step S26.

Then, a predetermined number n of cardiac periods is awaited, with a step S28. In that respect the Q-phases which occur are counted up to n before the procedure jumps back to step S16 in order to again check whether a magnetic triggering signal is still present. If that is the case, steps S20 through S28 are then carried out again. If however a magnetic triggering signal is no longer present, the procedure is terminated at step S18.

Figure 2:
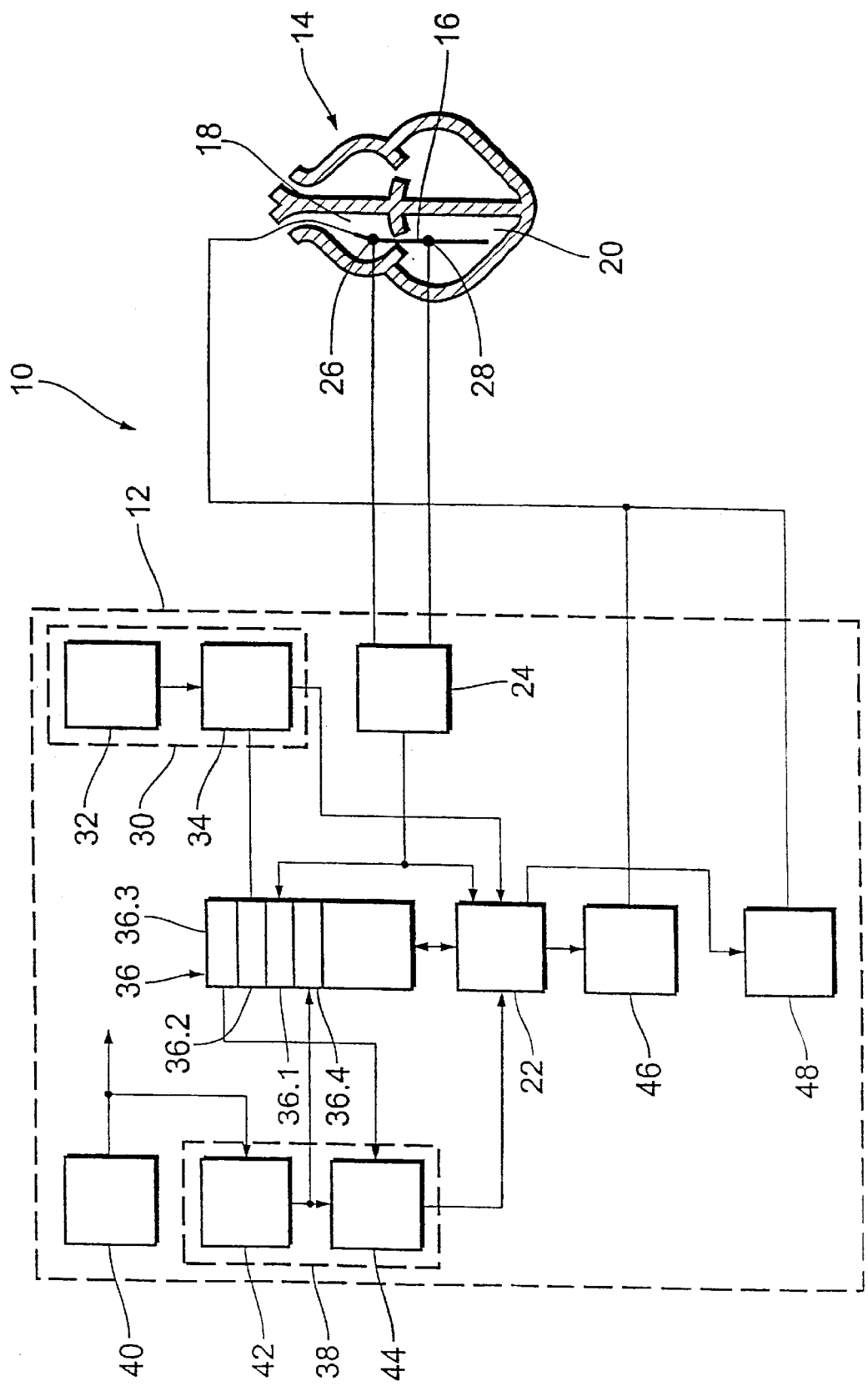
FIG. 2 is a diagrammatic view showing an ECG signal recorded during implementation of the method according to the invention.

FIG. 2 shows a simplified block circuit diagram of an embodiment of the cardiac stimulation device according to the invention. This involves an integrated cardioverter/defibrillator (ICD) 10 which in addition is adapted to implement a two-chamber pacemaker therapy. The ICD 10 is shown in the implanted condition.

The ICD 10 has an implantable pulse generator 12 and a stimulation electrode 16 which is connected thereto and which can be implanted in a heart 14. The stimulation electrode 16 is adapted to deliver stimulation pulses in the right atrium 18 and in the right ventricle 20.

The pulse generator 12 has a central control unit 22. It controls, co-ordinates and monitors the functional features of the pulse generator 12. It receives and processes for that purpose the signals and data from various measurement units.

Thus the control unit 22 is connected on the one hand to an electrocardiography (ECG) unit 24. The unit 24 records an intracardial electrocardiogram (IEGM) by means of two measurement electrodes 26 and 28 which are provided at the stimulation electrode 16. The measurement signal is passed to the control unit 22 for further processing. More details in this respect will be described hereinafter with reference to FIG. 3. At the same time the measurement signal, controlled by the control unit, can be stored in a region 36.1 of a storage means or memory 36 in order later if necessary to be called up for long-term evaluation.

On the other hand the control unit 22 receives signals and data from the telemetry unit 30. The telemetry unit 30 has a receiver 32 for magnetic signals of an external interrogation, programming and monitoring device (not shown). A comparator circuit 34 is connected to the receiver 32 and serves for identification of the detected magnetic signals. For that purpose the comparator circuit 34 accesses reference value and allocation tables stored in a storage region 36.2. After identification of the received signal the comparator circuit 34 signals to the control unit 22 which functional feature of the pulse generator 12 is being interrogated from the exterior.

Finally the control unit 22 receives signals from an EOL-indicator 38 (EOL=end of life) which monitors the energy content of a battery 40. The EOL-indicator 38 has a volt meter 42 connected to the output of the battery 40. The battery 40 serves for the energy supply for the pulse generator 12. A second comparator circuit 44 serves to compare the measured output voltage of the battery 40 to a reference value range stored in a storage region 36.3. If the output voltage falls below a lower threshold value which is predetermined by the threshold value range, the EOL-indicator 38 produces an EOL-signal which is passed to the control unit 22.

It will be appreciated that a plurality of value ranges in respect of the output voltage of the battery 40 can also be stored in the storage means in known manner and the second comparator circuit 44 can correspondingly produce differentiated signals. In that respect for example a first value range corresponds to the full functional capability of the battery, a second corresponds to an output voltage at which replacement of the battery soon is recommended (Elective Replacement Interval=ERI), and a third value range corresponds to an output voltage at which maintenance of the operation of the pulse generator is endangered.

Also connected to the control unit 22 are a pacemaker unit 46 and a cardioversion unit 48. Depending on the control signals received from the control unit 22, those units take over in known fashion the production and delivery of cardiac stimulation pulses and cardioversion or defibrillation pulses respectively.

Figure 3:
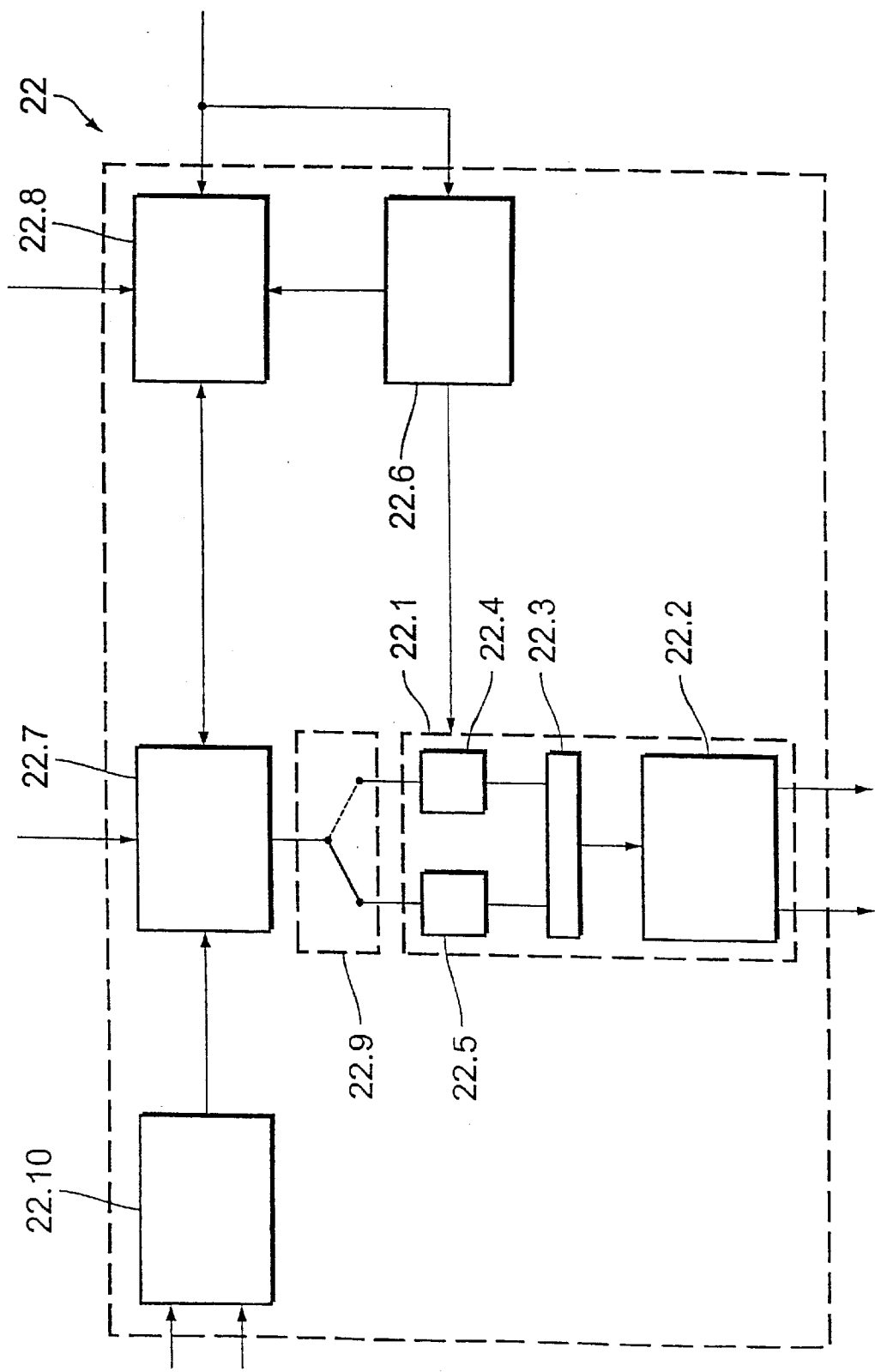
FIG. 3 shows a block circuit diagram of an embodiment of the cardiac stimulation device according to the invention.

FIG. 3 shows further details of the structural features of the control unit 22 which are essential for representing the invention, in the form of a simplified block circuit diagram.

The control unit 22 has a signal generator unit 22.1 with a signal generator 22.2. The signal generator is adapted to deliver control pulses to the pacemaker unit 46 or the cardioversion unit 48. A control pulse produced by the pulse generator causes the pacemaker unit 46 or the cardioversion unit 48 to directly produce and deliver a cardiac stimulation pulse. The receiver of the control pulse which is produced by the signal generator, that is to say either the pacemaker unit 46 or the cardioversion unit 48, is determined by means of an addressing device 22.3 connected upstream of the signal generator 22.2.

Connected upstream of the addressing device in parallel relationship are a trigger unit 22.4 and a time matching unit 22.5. These two are adapted to determine the moment in time of the delivery of a control pulse by the signal generator 22.2. The trigger unit 22.4 produces the control signals in accordance with a program which is predetermined by a therapy control unit 22.6, as is known from conventional ICDs with pacemaker functions. The time matching unit 22.5 is adapted to determine the moment in time of delivery of control pulses for the production of time-displaced cardiac stimulation pulses. For that purpose, method steps which were described with reference to FIG. 1 are implemented in the time matching unit 22.5.

It is to be noted however that the time matching unit is adapted not to deliver signal pulses but control signals to the signal generator 22.2. It determines the time of delivery of cardiac stimulation pulse and produces a corresponding control signal. The addressing device 22.3 ascertains from that control signal that the pacemaker unit 46 is to be actuated by the signal generator 22.2. The latter in turn ascertains from the control signal of the time matching unit 22.5 the moment in time at which the cardiac stimulation pulse is to be delivered, and causes same by delivery of a suitable pulse triggering signal to the pacemaker unit 46.

The time matching unit 22.5 accesses the output signal of a period duration measurement unit 22.6 which is referred to hereinafter for the sake of brevity as the T-measurement unit. The output signal of the T-measurement unit 22.6 indicates the spacing in respect of time between the last and penultimate Q-spikes and the moment in time at which the last Q-spike occurs. The output signal of the T-measurement unit 22.6 therefore contains near-time information about the period duration and the phase position of cardiac activity.

The time matching unit 22.5 determines the moment in time of delivery of a stimulation pulse by addition of the measured period duration to the moment in time at which the last Q-spike occurs and subsequent subtraction of a predetermined time displacement of for example 100 ms. The value of the time displacement can be predetermined by programming from the exterior and is stored in the storage device or memory 36.

A therapy control unit 22.7 monitors the state of the heart by means of a cardiac monitoring unit 22.8 and determines, by means of known diagnostic processes, what form of therapy is to be applied at the respective moment involved. The therapy control controls access to the trigger unit or the time matching unit in the manner of a change-over switching device 22.9. The time matching unit is actuated by the therapy control unit only when signaling to the exterior is to be implemented. For the purposes of carrying out the usual forms of therapy, the trigger unit 22.4 is operated by means of known therapy control procedures.

The therapy control unit 22.6 is additionally connected on the input side to an apparatus monitoring unit 22.10. The apparatus monitoring unit in turn receives the output signals of the first and second comparator circuits 34 and 44. If the second comparator circuit 44 indicates that the battery voltage is below the reference value range and at the same time the first comparator circuit 34 of the telemetry unit 30 indicates that the status of the battery is being interrogated from externally, the apparatus monitoring circuit 22.10 transmits the EOL- or ERI-signal from the comparator circuit 44 to the therapy control unit 22.7.

Upon reception of an EOL- or ERI-signal the therapy control unit 22.7 interrogates the heart monitoring unit 22.8 for the presence of a pathological state of the heart. If such a state is present, suitable therapy is initiated. When the heart is working normally—stimulated or in a natural rhythm—the time matching unit is activated by means of the change-over switching device 22.9.

It will be appreciated that in the same manner other internal statuses of the cardiac stimulation device can be signaled.

Figure 4:
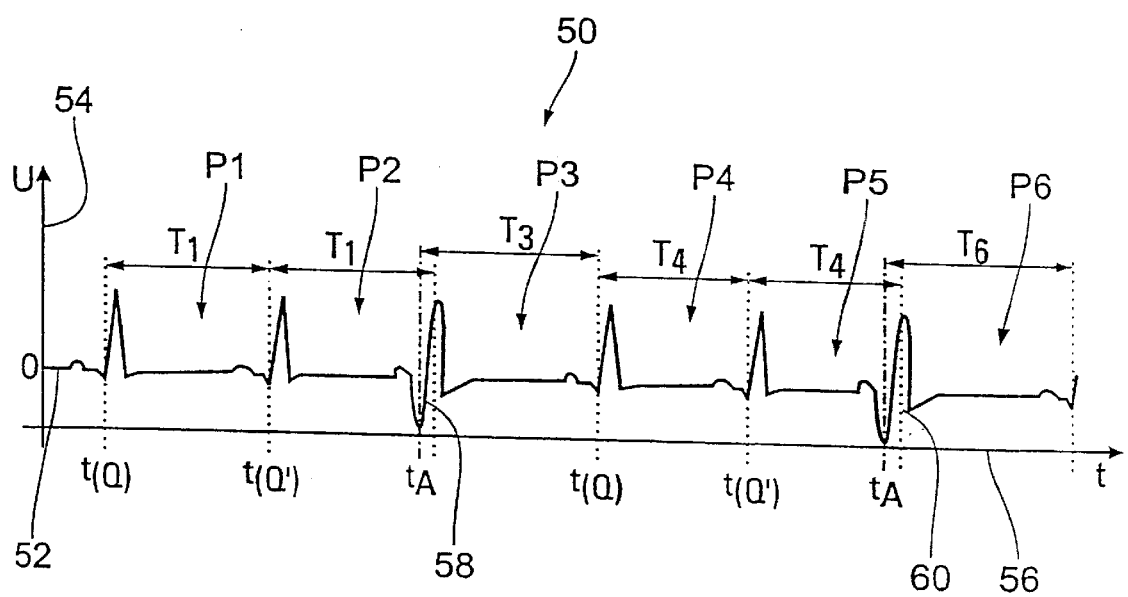
FIG. 4 shows a block circuit diagram of the control unit of the embodiment shown in FIG. 3.

FIG. 4 is a diagrammatic view showing an electrocardiogram 50 which was externally recorded during a signaling procedure by a cardiac stimulation device according to the invention. The time t is plotted on an abscissa 52 in units which are not specified in greater detail, while a measurement voltage U is plotted on an ordinate 54, also in undefined units.

A resulting ECG-curve 52 shows the known variation over the duration of five cardiac periods P1 through P5. The ECG-curve 52 reproduces the ECG of a natural cardiac activity. The period duration of the periods P1, P3 and P4 is characterized by arrow T1, T3, T4 and T6, the beginning and end points of which respectively coincide with the occurrence of a Q-spike in the ECG-curve 52.

The period durations of the periods P1 through P5 are not identical by virtue of the natural fluctuations in cardiac activity. In the present case T4 is somewhat shorter than T1, T3 and T6. Arrows characterized by the same references denote periods of time of equal length.

The beginning and end times of the periods P1 through P5 are identified by vertical broken lines. The beginning time of the period P1 is identified by t(Q) beneath the abscissa 56. That is the time of the occurrence of the Q-spike of the cardiac period P1. The time of the occurrence of the subsequent Q-spike is identified by t(Q').

When carrying out the method according to the invention by means of a cardiac stimulation device according to the invention, firstly the period of time T1 is determined in accordance with step S20 in FIG. 1 by the T-measurement unit 22.6 in FIG. 3. In the course of the initial phase of the cardiac period P2 the time matching unit 22.5 determines the triggering time $t_A$ for a signal pulse. This is additionally identified in FIG. 4 by a dash-dotted vertical line. The Figure shows a displacement of that dash-dotted line $t_A$ relative to the right-hand end of the arrow T1 which extends over the cardiac period P2. This therefore indicates when the period of time T1, that is to say the duration of the cardiac period P1, would expire again after the beginning of the period P2.

A strong deflection 58 towards negative voltage values can be seen in the ECG-curve 52, occurring at the time $t_A$. That deflection is the indication, which is visible in the ECG, of a cardiac stimulation pulse which is delivered by the pacemaker unit 46. That cardiac stimulation pulse can be distinguished from a regular, therapeutic cardiac stimulation pulse and can be identified as a signal pulse, by virtue of its time displacement relative to the time t(Q')+T1. This therefore indicates that the battery voltage of the cardiac stimulation device 10 has fallen below a reference value.

As the identification of only one signal pulse is not always unambiguous, the occurrence is repeated after two cardiac periods P4 and P5 in the cardiac period P6. Waiting for two periods without signaling corresponds to the step S28 of the method as shown in FIG. 1, wherein the number of two periods to be waited is stored in accordance with programming from the exterior in the storage device 36 (FIG. 2).

For the purposes of determining the triggering time $t_A$ in the period P6 the time matching unit 22.5 (FIG. 3) accesses the period duration T4 and the time t(Q') of the beginning of the period P5, which are determined by the T-measurement unit 22.6. The ECG-curve 52 correspondingly exhibits a second negative deflection 60.

That time pattern can also be seen in the ECG-curve 52 repeated for later times (not shown here) as long as the telemetry unit indicates external reception readiness for the signal and cardiac activity is normal.

What is claimed is:

1. A method of signaling an internal status of an implantable cardiac stimulation device, which status is defined by a value of a status parameter, comprising the steps of:
    recording a measurement value representing the status parameter;
    ascertaining the existence of the status by comparing the measurement value with a comparative value; and
    delivering a signal pulse with a predetermined, measurable pulse parameter, wherein the pulse parameter is uniquely associated with the status if the measurement value corresponds to the comparative value within predetermined limits;
    characterized by the following steps:
        measuring a time difference of equal, predetermined phases of two successive, periodically recurring sequences of events prior to delivery of the signal pulse; and then
        delivering the signal pulse prior to or after the next expiry of the measured time difference by a predeterminable period of time uniquely associated with the status.

2. The method of claim 1 wherein the method is started as soon as a triggering signal is present in the device.

3. The method of claim 2 wherein the method is carried out again if the triggering signal is still present after it has been carried out.

4. The method of claim 2 wherein the triggering signal is produced as long as a magnetic field with a predetermined magnetic field parameter is detected in the device.

5. The method of claim 3 wherein the triggering signal is produced as long as a magnetic field is detected in the device with a predetermined magnetic field parameter.

6. The method of claim 1, wherein no time-displaced signal pulse is produced subsequently to the delivery of the time-displaced signal pulse for a predeterminable number of subsequent sequences of events.

7. The method of claim 1 wherein measurement of a physical parameter is dependent on the phase of the cardiac cycle.

8. The method of claim 6 characterized by recording an electrocardiogram.

9. The method of claim 1, wherein the recorded measurement value is an electrical voltage at an output of an energy storage means arranged in the device.

10. The method of claim 1 wherein the delivered signal pulse is an electrical current pulse.

11. A stimulation device for a heart having a myocardium, comprising:
    a pulse generator for producing cardiac stimulation pulses;
    a stimulation electrode for delivering the pulses, the stimulation electrode being connected to the pulse generator;
    a signal generator for producing and delivering pulse triggering signals at defined moments in time, the signal generator being connected to the pulse generator;
    a cardiac phase measurement sensor for recording a first measurement value which is dependent on the current phase of the cardiac cycle; and
    means for measuring time to determine a cycle duration between the occurrence of a predetermined phase of a defined first cardiac cycle and the occurrence of the same phase of the directly subsequent second cardiac cycle, the means being connected to the cardiac phase measurement sensor;
    wherein a time matching means is provided to predetermine the period of time between the occurrence of the predetermined phase of the second cardiac cycle and the subsequent production of a pulse triggering signal, the time matching means being connected on an input side to the time measurement means and on an output side to the signal generator.

12. The device of claim 11, further comprising:
    a status measurement sensor for recording a status measurement value that depends on a current value of a status parameter of the device, the status measurement sensor being connected to the time matching means.

13. The device of claim 12, wherein the status measurement sensor is such that the status measurement value depends on the energy content of an energy storage device of the device.

14. The device of claim 12, further comprising:
    a means for receiving a comparative value for the status measurement value, the comparative value storage means being connected to the time matching means.

15. The device of claim 14, further comprising:
    a first means for comparing the status measurement value to the comparative value and producing and delivering a status signal that is dependent on the comparison result, the first comparison means being connected on an input side to the status measurement sensor and the comparative value storage means and on an output side to the time matching means.

16. The device of claim 15, further comprising:
    a monitoring unit for comparing the status signal to a pre-stored reference status value range and producing and delivering a waiting signal for the case that the status signal is not contained in the reference status value range, the monitoring unit being connected upstream of the time matching means and being connected on an input side to the first comparison means.

17. The device of claim 16, further comprising:
    an activation measurement sensor records an activation measurement value of an activation measurement parameter, the activation measurement sensor being connected to the time matching means.

18. The device of claim 17, wherein the activation measurement sensor is a magnetic field sensor.

19. The device of claim 18, further comprising:
    a pattern value storage means for recording a pattern value for the activation measurement value.

20. The device of claim 19, further comprising:
    a second means for comparing the activation measurement value to the pattern value and, in the case of coincidence, for producing and delivering a triggering signal, the second comparison means being connected on an input side to the activation measurement sensor and the pattern value storage means and on an output side to the time matching means.

21. The device of claim 20, wherein the monitoring unit is additionally connected at the input side to the second comparison means and is such that the waiting signal can be produced only when a triggering signal is present.

22. The device of claim 21, wherein:
the cardiac phase measurement sensor records a measurement signal which is dependent on the electrical polarization of the myocardium.

23. The device of claim 22, wherein:
the time measurement means determines the QQ-time interval of successive cardiac cycles.

24. The device of claim 23, wherein:
the time matching means produces the subsequent pulse triggering signal no earlier than 300 milliseconds prior to the expiry of the given cycle duration after the occurrence of the predetermined phase (Q') of the second cardiac cycle.

25. The device of claim 24, wherein:
the time matching means produces the subsequent pulse triggering signal no earlier than 200 milliseconds prior to the expiry of the given cycle duration after the occurrence of the predetermined phase (Q') of the second cardiac cycle.

26. The device of claim 25, wherein:
the time matching means produces the subsequent pulse triggering signal no later than 50 milliseconds prior to the expiry of the given cycle duration after the occurrence of the predetermined phase of the second cardiac cycle (Q').

27. The device of claim 26, wherein:
the time matching means produces the subsequent pulse triggering signal no later than 100 milliseconds prior to the expiry of the given cycle duration after the occurrence of the predetermined phase (Q') of the second cardiac cycle.

28. The device of claim 27, further comprising:
a pacemaker control means for selectively producing an activation or deactivation signal for respectively activating or deactivating operation of the time matching means, the pacemaker control means being connected to the time matching means.

29. The device of claim 28, wherein:
the pacemaker control means activates or deactivates operation of the time matching means for a predeterminable number of cardiac cycles, being connected on an input side to the cardiac phase measurement sensor.

30. The device of claim 29, wherein:
the pacemaker control means activates operation of the time matching means for the duration of a cardiac cycle and immediately subsequently deactivates operation of the time matching means.

31. The device of claim 30, wherein:
the pacemaker control means directly subsequently deactivates operation of the time matching means for the duration of at least two cardiac cycles.

32. The device of claim 31, wherein:
the pacemaker control means directly subsequently deactivates operation of the time matching means for the duration of at most 15 cardiac cycles.

33. The device of claim 28, further comprising:
a cardiac monitoring unit for comparing the respectively measured cycle duration to a reference cycle duration value range contained in a reference cycle value storage means, the cardiac monitoring unit being connected to the time measurement means upstream of the pacemaker control means.

34. The device of claim 33, wherein:
the cardiac monitoring unit, in the event of a deviation of the measured cycle duration from the reference cycle duration value range being present, produces a therapy warning signal which is dependent on the value of the deviation.

35. The device of claim 34, wherein:
the pacemaker control means produces and communicates a deactivation signal to the time matching means when a therapy warning signal is received.

36. The device of claim 35, wherein:
the pacemaker control means blocks the production of an activation signal for a defined period of time when a therapy warning signal is received.

37. The device of claim 36, further comprising:
a trigger unit for producing and delivering triggering signals to the signal generator at defined moments in time in the context of a pacemaker therapy, wherein the triggering signals cause the signal generator to produce and deliver pulse triggering signals, the trigger unit connected on an input side to the cardiac phase measurement sensor and on an output side to the signal generator.

38. The device of claim 37, wherein:
the pacemaker control means is additionally connected to the trigger unit and produces and delivers a trigger activation or deactivation signal to the trigger unit, wherein when a trigger activation signal is delivered to the trigger unit delivery of a deactivation signal to the time matching means also occurs and, vice-versa, when an activation signal is delivered to the time matching means, a trigger deactivation signal is also delivered to the trigger unit.

39. The device of claim 38, wherein:
the pacemaker control means produces a trigger activation signal when a therapy warning signal is present.

40. The device of claim 39, further comprising:
a cardioversion unit for producing and delivering stimulation pulses suitable for cardioversion or defibrillation at defined moments in time.

41. The device of claim 40, wherein:
the cardioversion unit is connected on an input side to the cardiac phase measurement sensor.

42. The device of claim 41, wherein:
the pacemaker control means is connected on an output side to the cardioversion unit and produces and delivers a cardioversion activation or deactivation signal.

43. The device of claim 42, wherein:
the pacemaker control means delivers a trigger de activation signal and a deactivation signal upon delivery of a cardioversion activation signal.

44. The device of claim 11, wherein:
the cardiac phase measurement sensor records a measurement signal which is dependent on the electrical polarization of the myocardium.

45. The device of claim 11, wherein:
the time measurement means determines the QQ-time interval of successive cardiac cycles.

46. The device of claim 11, wherein:
the time matching means produces the subsequent pulse triggering signal no earlier than 300 milliseconds prior to the expiry of the given cycle duration after the occurrence of the predetermined phase (Q') of the second cardiac cycle.

47. The device of claim 46, wherein:
the time matching means produces the subsequent pulse triggering signal no earlier than 200 milliseconds prior to the expiry of the given cycle duration after the occurrence of the predetermined phase (Q') of the second cardiac cycle.

48. The device of claim 11, wherein:

the time matching means produces the subsequent pulse triggering signal no later than 50 milliseconds prior to the expiry of the given cycle duration after the occurrence of the predetermined phase of the second cardiac cycle (Q').

49. The device of claim 48, wherein:

the time matching means produces the subsequent pulse triggering signal no later than 100 milliseconds prior to the expiry of the given cycle duration after the occurrence of the predetermined phase (Q') of the second cardiac cycle.

50. The device of claim 11, further comprising:

a pacemaker control means for selectively producing an activation or deactivation signal for respectively activating or deactivating operation of the time matching means, the pacemaker control means being connected to the time matching means.

51. The device of claim 50, wherein:

the pacemaker control means activates or deactivates operation of the time matching means for a predeterminable number of cardiac cycles, being connected on an input side to the cardiac phase measurement sensor.

52. The device of claim 51, wherein:

the pacemaker control means activates operation of the time matching means for the duration of a cardiac cycle and immediately subsequently deactivates operation of the time matching means.

53. The device of claim 52, wherein:

the pacemaker control means directly subsequently deactivates operation of the time matching means for the duration of at least two cardiac cycles.

54. The device of claim 53, wherein:

the pacemaker control means directly subsequently deactivates operation of the time matching means for the duration of at most 15 cardiac cycles.

55. The device of claim 54, wherein:

the pacemaker control means directly subsequently deactivates operation of the time matching means for the duration of 5 cardiac cycles.

56. The device of claim 54, wherein:

the pacemaker control means directly subsequently deactivates operation of the time matching means for the duration of 5 cardiac cycles.

57. The device of claim 50, further comprising:

a cardiac monitoring unit for comparing the respectively measured cycle duration to a reference cycle duration value range contained in a reference cycle value storage means, the cardiac monitoring unit being connected to the time measurement means upstream of the pacemaker control means.

58. The device of claim 57, wherein:

the cardiac monitoring unit, in the event of a deviation of the measured cycle duration from the reference cycle duration value range being present, produces a therapy warning signal which is dependent on the value of the deviation.

59. The device of claim 58, wherein:

the pacemaker control means produces and communicates a deactivation signal to the time matching means when a therapy warning signal is received.

60. The device of claim 59, wherein:

the pacemaker control means blocks the production of an activation signal for a defined period of time when a therapy warning signal is received.

61. The device of claim 50, further comprising:

a trigger unit for producing and delivering triggering signals to the signal generator at defined moments in time in the context of a pacemaker therapy, wherein the triggering signals cause the signal generator to produce and deliver pulse triggering signals, the trigger unit connected on an input side to the cardiac phase measurement sensor and on an output side to the signal generator.

62. The device of claim 61, wherein:

the pacemaker control means is additionally connected to the trigger unit and produces and delivers a trigger activation or deactivation signal to the trigger unit, wherein when a trigger activation signal is delivered to the trigger unit delivery of a deactivation signal to the time matching means also occurs and, vice-versa, when an activation signal is delivered to the time matching means, a trigger deactivation signal is also delivered to the trigger unit.

63. The device of claim 62, wherein:

the pacemaker control means produces a trigger activation signal when a therapy warning signal is present.

64. The device of claim 11, further comprising:

a cardioversion unit for producing and delivering stimulation pulses suitable for cardioversion or defibrillation at defined moments in time.

65. The device of claim 64, wherein:

the cardioversion unit is connected on an input side to the cardiac phase measurement sensor.

66. The device of claim 65, wherein:

the pacemaker control means is connected on an output side to the cardioversion unit and produces and delivers a cardioversion activation or deactivation signal.

67. The device of claim 66, wherein:

the pacemaker control means delivers a trigger deactivation signal and a deactivation signal upon delivery of a cardioversion activation signal.

* * * * *